(12) United States Patent
Volckaerts (10) Patent No.: US 8,679,031 B2
(45) Date of Patent: Mar. 25, 2014

(54) HEARING PROSTHESIS WITH INTEGRATED SENSORS FOR MEASURING PRESSURE IN A COCHLEA

(75) Inventor: Bart Volckaerts, Borgerhout (BE)

(73) Assignee: Cochlear Limited (AU)

( * ) Notice: Subject to any disclaimer, the term of this patent is extended or adjusted under 35 U.S.C. 154(b) by 132 days.

(21) Appl. No.: 13/161,460

(22) Filed: Jun. 15, 2011

(65) Prior Publication Data
US 2011/0245714 A1 Oct. 6, 2011

Related U.S. Application Data

(63) Continuation-in-part of application No. PCT/AU2009/001634, filed on Dec. 16, 2009.

(30) Foreign Application Priority Data

Dec. 16, 2008 (AU) ............................... 2008906479

(51) Int. Cl.
*A61B 5/00* (2006.01)
*A61N 1/36* (2006.01)
*H04R 25/00* (2006.01)

(52) U.S. Cl.
CPC .......... *A61N 1/36032* (2013.01); *H04R 25/606* (2013.01)
USPC ............................................ 600/559; 607/57

(58) Field of Classification Search
USPC .................... 600/559–561; 607/137
See application file for complete search history.

(56) References Cited

U.S. PATENT DOCUMENTS

| 5,061,282 | A | | 10/1991 | Jacobs | |
|---|---|---|---|---|---|
| 5,443,493 | A | * | 8/1995 | Byers et al. | 607/137 |
| 5,531,787 | A | * | 7/1996 | Lesinski et al. | 623/10 |
| 5,645,585 | A | * | 7/1997 | Kuzma | 623/10 |

(Continued)

FOREIGN PATENT DOCUMENTS

| CN | 1613437 A | 5/2005 |
|---|---|---|
| CN | 101081188 A | 12/2007 |

(Continued)

OTHER PUBLICATIONS

Park et al. "Sub-MM Encapsulated Accelerometers: A fully Implantable Sensor for Cochlear Implants", 13th international conference on Solid-State Sensors, Actuators and Microsystems, Seoul, Korea, Jun. 5-9, 2005.*

(Continued)

*Primary Examiner* — Jeffrey G Hoekstra
*Assistant Examiner* — Michael C Stout
(74) *Attorney, Agent, or Firm* — McDonnell Boehnen Hulbert & Berghoff LLP (57) ABSTRACT

The present application discloses a hearing prosthesis comprising a stimulation assembly configured to be implanted into a cochlea. The stimulation assembly comprises a plurality of electrodes and one or more sensors. The one or more sensors may be configured to measure pressure within the cochlea. The pressure measurements may include (i) measurements of pressure corresponding to a physical contact of the one or more sensors with internal cochlear structures, (ii) measurements of perilymph fluid pressure, or (iii) measurements of pressure waves in the perilymph fluid corresponding to external sound waves. In one aspect, the sensor may be used by a system to help surgeons avoid damage to the cochlea during surgical implantation of the stimulation assembly. In another aspect, the sensor may be one component of an implantable microphone.

7 Claims, 4 Drawing Sheets

(56) References Cited

U.S. PATENT DOCUMENTS

| | | | |
|---|---|---|---|
| 5,792,072 A * | 8/1998 | Keefe | 600/559 |
| 5,792,073 A * | 8/1998 | Keefe | 600/559 |
| 6,007,494 A * | 12/1999 | Zenner et al. | 600/559 |
| 6,157,861 A * | 12/2000 | Faltys et al. | 607/57 |
| 6,216,040 B1 | 4/2001 | Harrison | |
| 6,259,951 B1 | 7/2001 | Kuzma et al. | |
| 6,342,035 B1 | 1/2002 | Kroll et al. | |
| 6,491,644 B1 | 12/2002 | Vujanic et al. | |
| 7,580,754 B2 * | 8/2009 | Zhang et al. | 607/55 |
| 7,618,450 B2 | 11/2009 | Zarowski et al. | |
| 7,856,274 B2 * | 12/2010 | Mechlenburg et al. | 607/42 |
| 7,856,275 B1 * | 12/2010 | Paul et al. | 607/55 |
| 8,285,384 B2 * | 10/2012 | Ball et al. | 607/57 |
| 8,287,462 B2 * | 10/2012 | Givens et al. | 600/559 |
| 2002/0072781 A1 * | 6/2002 | Lattner et al. | 607/42 |
| 2003/0144603 A1 * | 7/2003 | Zoth et al. | 600/559 |
| 2003/0220585 A1 * | 11/2003 | Hissong | 600/560 |
| 2004/0215236 A1 * | 10/2004 | Lattner et al. | 607/2 |
| 2005/0163333 A1 | 7/2005 | Abel et al. | |
| 2005/0177204 A1 | 8/2005 | Zhang et al. | |
| 2005/0245990 A1 * | 11/2005 | Roberson | 607/57 |
| 2007/0156063 A1 * | 7/2007 | Zoth et al. | 600/559 |
| 2007/0161848 A1 | 7/2007 | Dalton et al. | |
| 2007/0161875 A1 * | 7/2007 | Epley | 600/301 |
| 2007/0282397 A1 * | 12/2007 | Ball et al. | 607/57 |
| 2008/0194984 A1 * | 8/2008 | Keefe | 600/559 |
| 2008/0275292 A1 * | 11/2008 | Lattner et al. | 600/26 |
| 2008/0275293 A1 * | 11/2008 | Lattner et al. | 600/26 |
| 2008/0275513 A1 * | 11/2008 | Lattner et al. | 607/2 |
| 2009/0097681 A1 * | 4/2009 | Puria et al. | 381/318 |
| 2010/0041961 A9 * | 2/2010 | Epley | 600/301 |
| 2012/0059274 A1 * | 3/2012 | Zoth et al. | 600/547 |

FOREIGN PATENT DOCUMENTS

| | | |
|---|---|---|
| WO | 97/18689 A1 | 5/1997 |
| WO | 2004/018980 A2 | 3/2004 |
| WO | 2009/152528 A1 | 12/2009 |

OTHER PUBLICATIONS

Wise et al. "Integrated sensors, MEMS, and microsystems:Reflections on a fantastic voyage" Sensors and Acutators A 136 (2007) 39-50.*

* cited by examiner

HEARING PROSTHESIS WITH INTEGRATED SENSORS FOR MEASURING PRESSURE IN A COCHLEA

CLAIM OF PRIORITY

The present application for patent is a continuation-in-part of PCT Application PCT/AU2009/001634 entitled "Implantable Microphone," filed 16 Dec. 2009, and currently pending. PCT Application PCT/AU2009/00163 claims priority to Australian Provisional Patent Application No. 2008906479, filed 16 Dec. 2008. The present application for patent also claims priority to Australian Provisional Patent Application No. 2008906479 entitled "IMPLANTABLE MICROPHONE", filed 16 Dec. 2008. The entire contents of Australian application 2008906479 and PCT application PCT/AU2009/001634 are hereby expressly incorporated by reference herein in their entirety.

TECHNICAL FIELD

The present application discloses certain features of an implantable hearing prosthesis such as a cochlear implant. In one embodiment, the hearing prosthesis includes a stimulation assembly comprising a plurality of electrodes and at least one sensor. The at least one sensor may be configured to measure pressure within a cochlea. The sensor may be used as a component of an implantable microphone for the hearing prosthesis. The sensor may also be used to measure pressure within the cochlea during the surgical implantation of the stimulation assembly of the hearing prosthesis.

INCORPORATION BY REFERENCE

The entire contents of each of the following documents are hereby incorporated by reference:
U.S. Pat. Nos. 4,532,930; 6,537,200; 6,565,503; 6,575,894; 6,697,674; and 5,758,651;
PCT Publication No. WO 2005/122887; and
PCT Publication No. WO/209102811

BACKGROUND

Use of hearing devices such as external hearing aids, implanted hearing aids, cochlear implants, middle ear implants and electro-acoustic devices are widely used to deliver hearing capability to recipients. Typically, implantable hearing aids like cochlear implants are semi-implantable in that they comprise an implant with an electrode or a transducer and an external part. This external part typically comprises a hearing aid like device, which houses one or more microphones, a speech processor and the battery. The external device sends power and data to the implant via a transmitter coil. The transmitter coil and implant are positioned relative to each other by two magnets which reside in each component.

An important development in these types of hearing devices is the adaptation to a totally implantable form where these devices have no external components. This is seen to have a number of important advantages including being more aesthetically pleasing to the recipient as no components such as a microphone are required to be worn externally by the recipient. These fully implantable devices also have the advantages of being inherently waterproof and of providing hearing capability even while the recipient is sleeping, thereby providing an added safety benefit.

An important requirement of a fully implantable hearing device is the use of an implantable microphone or other sound detection device that functions to receive sound and process this into an electrical signal to drive the hearing prosthesis. A typical example of an implantable, subcutaneous, microphone involves the coupling of a transducer (e.g. electret, piezo or other pressure sensitive transducer) to an open ended cavity or acoustic volume located in a shell casing or housing formed from titanium, where the acoustic volume is covered by a diaphragm also typically formed from titanium. The diaphragm diameter and thickness and acoustic volume are then optimised to maximise the signal level after implantation. The subcutaneous microphone is also hermetically sealed so as not to present an infection risk to the recipient or otherwise expose the recipient to any toxic materials that the microphone is formed of.

Implantable microphones of this type have a number of associated disadvantages. As the subcutaneous microphone is covered by a layer of skin or tissue this directly attenuates the external sound resulting in a deterioration of the microphone's performance. More importantly, the skin layer decreases the resonance frequency of the diaphragm, since it will behave as a spring mass system. Due to this shift in resonance frequency the overall bandwidth of the microphone is reduced. Apart from the direct attenuation of external sound, there are a number of sources of noise in addition to the standard electrical noise associated with the electrical components which can also significantly degrade the performance of an implanted microphone. As the diaphragm is mass loaded, sitting under a layer of tissue or skin, it is sensitive to body induced vibrations transmitted typically via the skull which originate from the recipient's chewing, breathing, muscle movements, speaking, etc.

Another example of an implantable microphone involves direct measurement of components of the middle ear. In systems of this type, a sensor is implanted into the ear at a location to measure the mechanical vibration of one or more of the ossicles (i.e. the malleus, incus and stapes). Vibration sensors mounted to the ossicles are able to take advantage of extracting sound information from the natural auditory pathway, thereby potentially capturing a more natural sound spectrum at an improved signal to noise ratio. However, this approach has the significant disadvantage that more complex surgery is required for the recipient due to the additional fixation of the sensor to the middle ear.

It is desirable to improve upon any one or more of the above identified shortcomings.

SUMMARY

A hearing prosthesis according some embodiments may include a stimulation assembly configured to be implanted into a cochlea. The stimulation assembly may include a plurality of electrodes and at least one sensor. The sensor may be configured to measure pressure within the cochlea. The pressure measurements may include: (i) measurements of pressure corresponding to a physical contact of the sensor with internal cochlear structures, (ii) measurements of perilymph fluid pressure, or (iii) measurements of pressure waves in the perilymph fluid corresponding to external sound waves. In one aspect, the sensor may be used by a system to help surgeons avoid damage to the cochlea during surgical implantation of the stimulation assembly. In another aspect, the sensor may be one component of a microphone.

The stimulation assembly may include a proximal end and a distal end. The distal end of the stimulation assembly may be operable to be inserted into the cochlea on implantation. In some embodiments, the sensor may be located at or near the distal end of the stimulation assembly.

In some embodiments, the sensor may be an optical based sensor. In optical sensor embodiments, the optical sensor may include a light source for emitting light; a waveguide member for propagating emitted light to the optical sensor and/or for receiving reflected light from the optical sensor; and a detector for measuring intensity fluctuations in the reflected light, the intensity fluctuations in the reflected light corresponding to pressure variations in the perilymph sensed by the sensor.

In some embodiments, the waveguide member may be an optical fibre portion. The optical fibre portion may extend along the stimulation assembly.

In some embodiments, the sensor may include a flexible member operative to flex in accordance with pressure variations in the perilymph. An internal side of the flexible member may be arranged to reflect emitted light from the light source. The flexible member may be substantially hemispherical in some embodiments.

In some optical sensor embodiments, the optical sensor may include a transparent window including a partially reflective surface arranged to allow light from the light source to pass through the transparent window and the partially reflective surface. In some embodiments, the flexible member may be substantially parallel to and separated by a gap from the partially reflective surface to form a Fabry-Perot sensor. Other embodiments may incorporate or utilize other optical interferometer configurations.

In some embodiments, a plurality of sensors may be located along the stimulation assembly. One or more of the plurality of sensors may be spaced along the electrode assembly. In some embodiments, sensors may be aligned with corresponding electrodes located along the electrode assembly.

In some embodiments, the sensor may be used to monitor pressure inside the cochlea while a surgeon is inserting the stimulation assembly into the cochlea. The present application discloses methods of measuring cochlear pressure with the sensor during the insertion of a stimulation assembly of the hearing prosthesis into a cochlea, and generating an indication in response to determining that the measured pressure is likely to cause cochlear damage. Some embodiments may include measuring cochlear pressure with multiple sensors during the insertion of the stimulation assembly of the cochlear implant into the cochlea.

BRIEF DESCRIPTION OF THE DRAWINGS

Illustrative embodiments will be discussed with reference to the accompanying drawings wherein.

In the following description, like reference characters designate like or corresponding parts throughout the several views of the drawings.

DETAILED DESCRIPTION

Before describing the features of the disclosed embodiments, it is convenient to briefly describe the overall construction and operation of a typical cochlear implant system.

Figure 1:
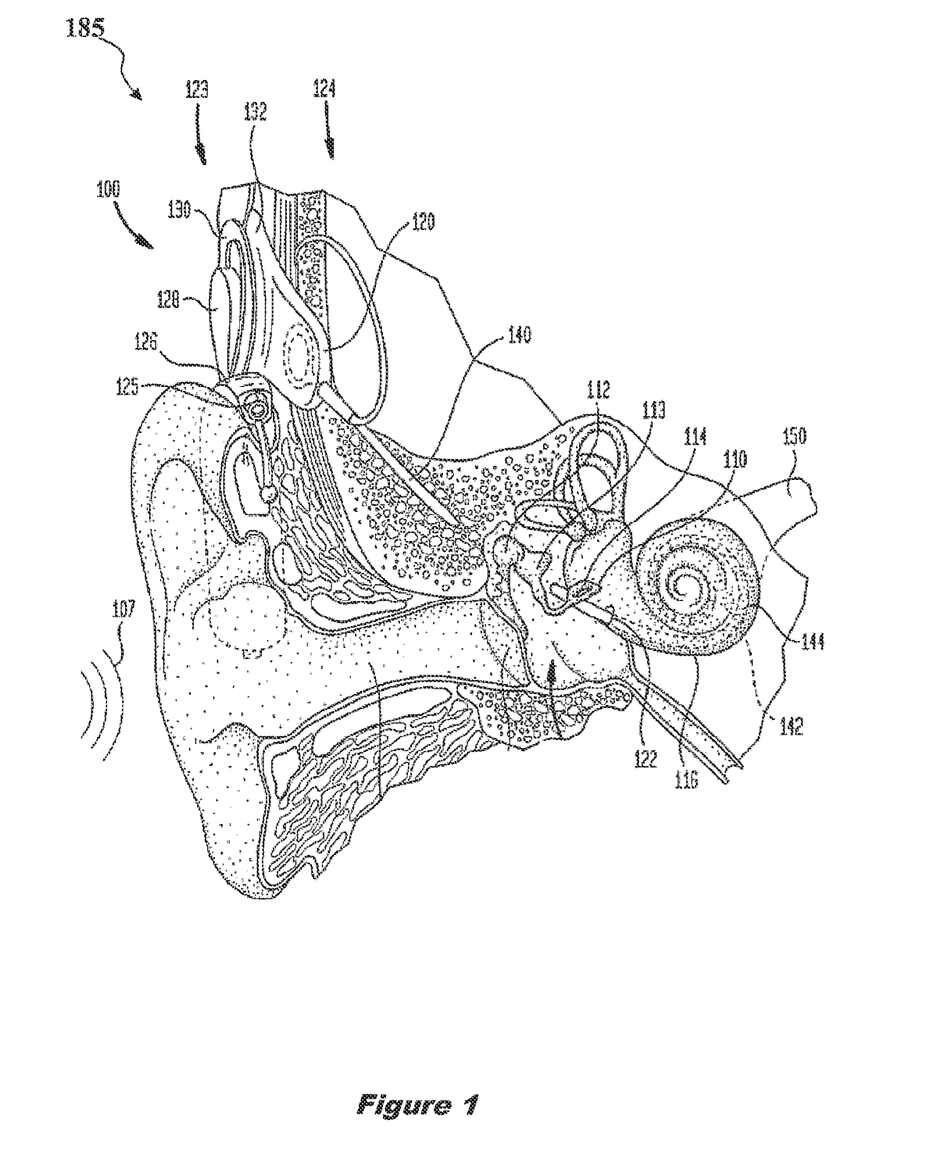
FIG. 1 is a simplified schematic view of a conventional cochlear implant system.

Referring to FIG. 1, cochlear implant system 185 comprises external component assembly 100 and internal (or implanted) component assembly 124. External assembly 100 comprises a behind the ear (BTE) speech processing unit or speech processor 126 connected to a transmission coil 130. Speech processor 126 includes an external microphone 125 for detecting sound and generating an electrical signal which is then processed by electronics within the speech processor 126 to generate coded signals. The coded signals are provided to an external transmitter unit 128, along with power from a power source such as a battery (not shown).

The internal component assembly 124 includes a receiver unit 132 having an internal coil (not shown) that receives and transmits power and coded signals from external assembly 100 to a stimulator unit 120 to apply the coded signal along an electrode lead 140 to an electrode assembly 144 comprising a plurality of electrodes 142 where each electrode comprises an electrode or stimulation contact and an electrode wire (not shown) which can be independently stimulated. Electrode assembly 144 is inserted into the cochlea 116 in an implantation procedure known as cochleostomy and in this example, the electrode assembly 144 is inserted into the scala tympani through an incision 122 in the wall of the cochlea with the electrodes 142 positioned to be substantially aligned with the basilar membrane portions of the cochlea 116 as described below.

The cochlea 116 is tonotopically mapped with different regions extending along the cochlea 116 being responsive to acoustic and/or stimulus signals in different frequency ranges. As one of ordinary skill in the art is aware, low frequency sounds stimulate the basilar membrane of the cochlea 116 most significantly at its apex, while higher frequencies more strongly stimulate the basilar membrane at the cochlea's base. To accommodate this property of the cochlea 116, the electrode assembly 144 is constructed and arranged to deliver suitable stimulating signals to individual basilar membrane portions of the cochlea 116 in accordance with the different frequency components of a received audio signal 107, thereby stimulating the auditory nerve 150. Thus, electrodes 142 of electrode assembly 144 located near the base of the cochlea are used to simulate high frequency sounds while electrodes 142 closer to the apex are used to simulate lower frequency sounds. It should be appreciated that although in FIG. 1 the electrodes 142 in electrode assembly 144 are arranged as a linear array other arrangements are possible.

Further details of the above and other exemplary cochlear implant systems in which the disclosed embodiments can be implemented include, but are not limited to, systems described in U.S. Pat. Nos. 4,532,930; 6,537,200; 6,565,503; 6,575,894; 6,697,674; 5,758,651; and WO 2005/122887, each of which are hereby incorporated by reference in their entireties.

Figure 2:
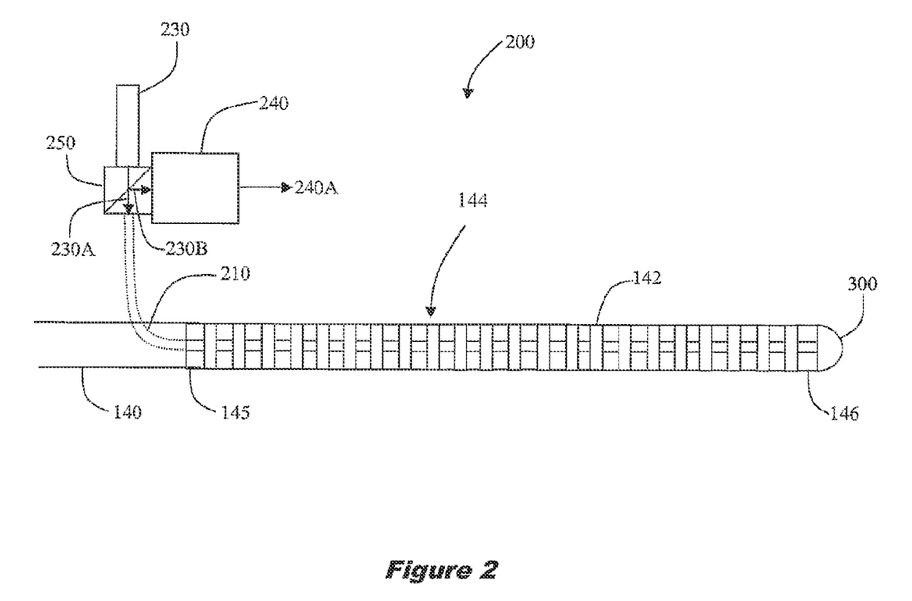
FIG. 2 is a figurative view of a stimulation assembly comprising an electrode array and a sensor according to an illustrative embodiment.

Referring now to FIG. 2, there is shown a stimulation assembly 140 of a cochlear implant. The stimulation assembly 140 comprises an electrode assembly 144 and a sensor 300 configured to measure pressure within a cochlea. In one application, the sensor 300 can be used to monitor pressure within the cochlea during the surgical procedure while the stimulation assembly 148 is being inserted into a cochlea by a surgeon. After the stimulation assembly 148 has been implanted into the cochlea, the cochlear implant may be configured to use the sensor 300 as a component of an implantable microphone 200. In operation, the cochlear implant may be configured to convert one or more pressure measurements (e.g., measurements of pressure waves in the perilymph within the scala tympani corresponding to external sound waves) from the sensor 300 into electrical stimulation signals for application to the cochlea via the electrode assembly 144 as described herein.

A stimulation assembly of a cochlear implant comprising a sensor 300 configured for use as an implantable microphone 200 in accordance with an illustrative embodiment is shown in FIG. 2. In this illustrative embodiment, implantable microphone 200 includes a sensor 300 that is integrated with the stimulation assembly 140. While in this illustrative embodiment, stimulation assembly 140 is comprised of a plurality of electrodes 142 thereby forming an electrode assembly 144 similar to that described with reference to FIG. 1 where the cochlea implant would be typically inserted into the scala tympani of the recipient. It would be appreciated by those of ordinary skill in the art that stimulation assembly 140 may also include other neural stimulating devices such as those based on delivering electromagnetic radiation to nerve cells to generate neural activity.

Figure 3:
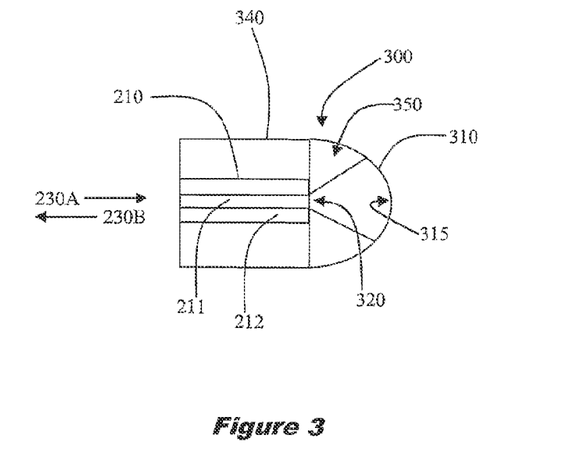
FIG. 3 is an enlarged view of the sensor located at the end of the stimulation assembly illustrated in FIG. 1.

In this illustrative embodiment, implantable microphone 200 includes an elongate fibre portion 210 having a core 211 and cladding region 212 (as best seen in FIG. 3) that extends from the proximal end 145 of stimulation assembly 140 and terminates in sensor 300 located at the distal end 146 of stimulation assembly 140. At the input end of fibre portion 210 there is located a compact light source 230 such as a light emitting diode (LED) or a vertical cavity surface emitting laser (VCSEL) which is a type of semiconductor laser diode having laser beam emission perpendicular from a top surface of a metal contact. Other types of light sources may be used. Specifically, any light source that meets the shape, size, wavelength and/or intensity demands of the specific embodiment may be employed as required. Some other example light sources include, but are not limited to, laser diodes or microlasers such as the VCSEL laser referred to above and other laser types including free electron lasers (FELs), etc.

Implantable microphone 200 further includes in this embodiment an optical beam splitter 250 and a detector 240 such as a photodiode which functions to detect the intensity of light reflected by sensor 300 and provide a detected electrical signal 240A for further processing by the cochlear implant system to generate stimulating signals to be delivered by stimulation assembly 148 to the cochlea.

As would be appreciated by those of ordinary skill in the art, the configuration of implantable microphone 200 as depicted in FIGS. 2 and 3 is but one example of a suitable arrangement for sensing pressure variations in the cochlea and perilymph involving a sensor that is integrated into stimulation assembly 140. As an example, in other embodiments, one or more sensors 300 may be deployed at various locations along the stimulation assembly 140 depending on requirements. Additionally, one or more of the components of this embodiment of implantable microphone 200 such as the compact light source 230, beam splitter 250 or detector 240 may be integrated into the stimulation assembly 140. In one illustrative embodiment, light source 230 may be located to directly emit light onto sensor 300 which is then in turn reflected and propagated along fibre portion 210 to detector 240 which is located at a different location either integrated into or external to stimulation assembly 140.

Fibre portion 210 may be constructed of any suitable material and in this illustrative embodiment comprises a low bending-loss silica or plastic fibre having a doped core and an outer cladding diameter of approximately 10 μm and 125 μm, respectively. As would be appreciated by those skilled in the art, fibre portion 210 may comprise any suitable waveguide member that functions to propagate light along its length including, but not limited to, fibres having nanoscale structured cores (e.g. of the order 50 nm). Other types of optical fibres may also be suitable for fibre portion 210 including those formed from glass (silica) or polymers having high refractive indices, such as Polyethersulfone (PES) and Polyhenylsulfone (PPS) and including examples such as low bending loss fibres, photonic crystal fibres, telecommunication fibres, metal coated silica core fibres, etc.

In some embodiments, where the optical fibre includes materials such as doping elements that are non-biocompatible, fibre portion 210 is hermetically sealed. Materials which may be used to hermetically seal fibre portion 210 include, for example, parylene, diamond-like carbon, and platinum. In other embodiments, fibre portion or waveguide member 210 may support many propagation paths or transverse modes. Waveguide structures of this type are referred to as multimode and in particular optical fibres of this type are referred to as multimode fibres (MMF). In contrast, fibres or waveguide structures which support only a single mode are called single mode fibers (SMF). Embodiments may use either a single mode or multimode waveguides or fibres.

Furthermore, as the terms are used herein, a fibre portion or waveguide member is an inclusive term that covers both a unitary structure such as a single optical fibre as well as multiple structures such as a bundle of individual optical fibres, a fused bundle of optical fibres, star couplers. Furthermore, these terms may also include the ferrules, lenses, and other structures used to couple light into and out of the optical fibres or other waveguide structures.

It should be appreciated that although FIGS. 2 and 3 and other embodiments referred to herein illustrate the use of one type of fibre portion 210 to propagate light to and from sensor 300, other types of waveguide member such as has been described above could be used in alternative embodiments. In another exemplary embodiment, the carrier member of stimulation assembly 140 is modified to function as a waveguide member by lining a central channel or bore extending through the carrier member with a reflecting layer to cause total internal reflection and thereby minimise the loss or spread of light.

Referring now to FIG. 3, there is shown an enlarged view of sensor 300 which comprises a hemispherical flexible membrane 310 having an internal reflective surface 315 which reflects light emitted from the output end 320 of fibre portion 210. In this illustrative embodiment, flexible membrane 310 may be made from titanium or platinum or other biocompatible material such as a polymer coated with a suitable reflection coating and is attached to support structure 340 which receives the output end 320 of fibre portion 210. In some embodiments, the flexible membrane 310 may have an outer covering of a flexible or elastic material configured to flex in response to changes in pressure within the cochlea, such as changes in pressure when the outer covering touches a cochlear structure or changes in the perilymph fluid pressure within the cochlea.

In this illustrative embodiment, the thickness of flexible membrane 310 will typically vary between 20 μm and 1 mm and will depend on the material selected and be optimised in accordance with the requirement to experience large deflections to generate significant deviations of the back reflected light beam 230B at detector 240. The internal region 350 bounded by support structure 340, the output end 320 of fibre portion 210 and flexible membrane 310 may be filled with an inert gas or a gel having a refractive index matched to the core 211 of fibre portion 210 to ensure efficient coupling between light reflected from flexible membrane 310 and core 211.

In operation, emitted light 230A emanating from light source 230 travels along fibre portion 210 and is emitted from output end 320 where it is then reflected by the internal reflective surface 315 of flexible membrane 310 resulting in reflected light 230B travelling in the reverse direction along fibre portion 210 where it is directed by beam splitter 250 into light detector 240. As flexible membrane 310 flexes and changes its configuration in accordance with pressure variations in the perilymph the intensity of reflected light 230B will vary.

Figure 6:
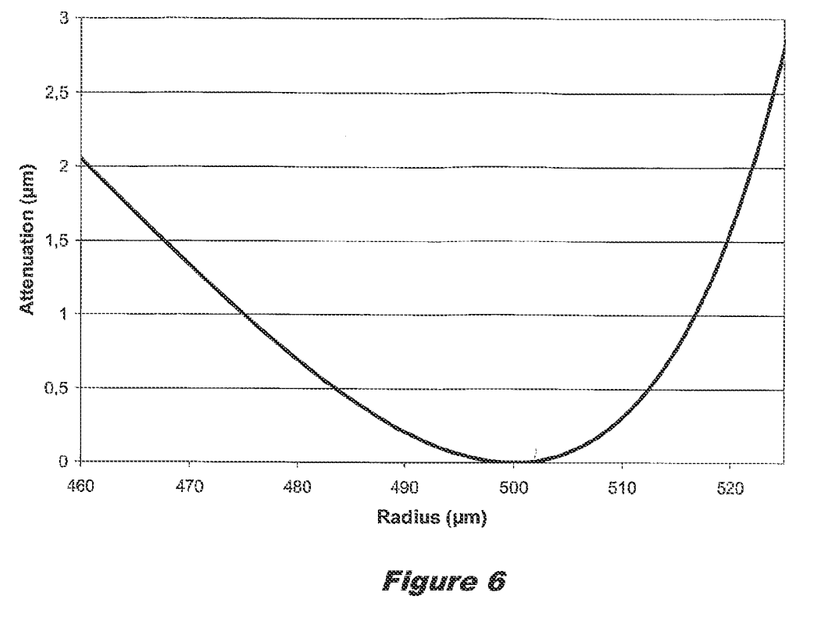
FIG. 6 is a graph of the performance of the sensor element illustrated in FIG. 3.

Referring now to FIG. 6, there is shown the results of a calculation based on ray transfer matrix analysis for a sensor 300 as illustrated in FIG. 3, having a flexible membrane 310 of thickness 20 μm and a radius of curvature of 500 μm with the assumption that internal region 350 was filled with an index matching material. As can be seen, small deviations in the radius of curvature of flexible membrane 310 will result in an attenuation of 2 dB of the light beam that is back reflected into the fibre end 320 and finally recorded by photodetector 240.

As discussed previously, the intensity fluctuations in reflected light 230B are measured by detector 240 which generates an electrical signal 240A which corresponds to these pressure variations in the perilymph pressure. These electrical signals can then be processed by the speech processor or equivalent component of the cochlear implant system.

While in this illustrative embodiment, flexible membrane 310 is hemispherical in shape to maximise the amount of reflected light 230B, equally the flexible membrane may be of a generally flat configuration or alternatively adopt other regular or irregular shapes or combinations thereof as required to provide a flexible member that flexes in accordance with pressure variations in the perilymph.

Figure 4:
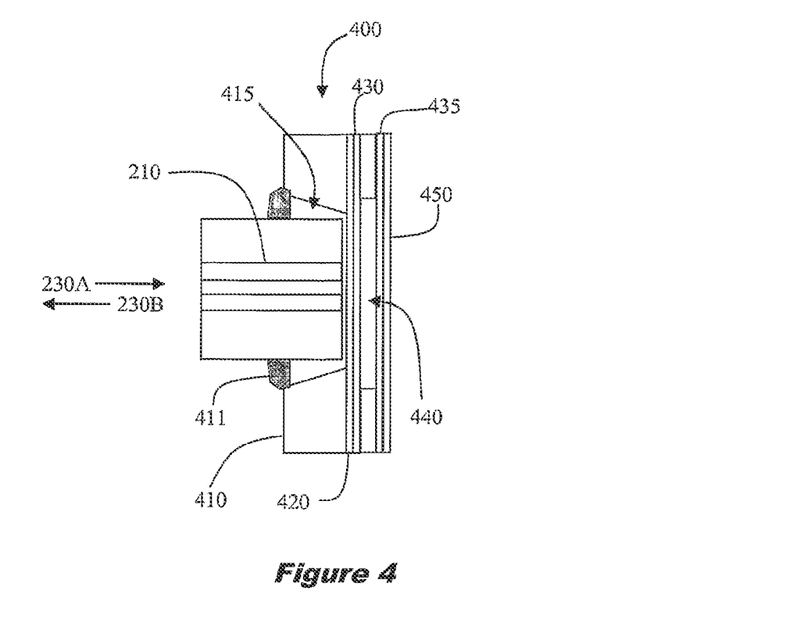
FIG. 4 is a figurative view of a sensor for an implantable microphone in accordance with an illustrative embodiment.

Referring now to FIG. 4, there is shown a sensor 400 in accordance with another illustrative embodiment of implant microphone. In this embodiment, sensor element 400 is configured as a Fabry-Perot interferometer including an alignment block 410 which may be fabricated from a rigid material such as silicon or a suitable polymer. Alignment block 410 functions to receive the end of fibre portion 210 into a tapered receiving channel 415 which is sealed by sealing epoxy 411 and provides a stable platform for transparent window 420, partially reflective surface 430 which is formed from a dielectric mirror material and flexible membrane 450 having an inner reflective surface 435 which in this illustrative embodiment is also formed from a dielectric mirror material.

Dielectric mirrors 430, 435 each comprise a stack of thin dielectric layers featuring different refractive indices, the combination of which are optimised to provide a predetermined reflectance at a given wavelength and inclination angle. Flexible membrane 450 is once again formed from a biocompatible material such has been described previously and will have a thickness optimised in accordance with the type of material and the desired performance of the sensor element 400. Between dielectric mirror 430 and the internal reflective surface 435 of flexible membrane there is provided an air gap 440 having a controlled spacing in the order of the wavelength of the light source (i.e. approximately 1 μm in this exemplary embodiment).

In operation, emitted light 230A emanating from light source 230 travels along fibre portion 210 and is transmitted through transparent window 420 and partially reflective mirror 430 where it will undergo multiple internal reflections as it is reflected from dielectric mirror 435 of flexible membrane 450. As the overall reflectance will be dependent on the spacing of air gap 440, any flexing of flexible membrane 450 will cause a change in reflectance of sensor element 400 and hence the amount of reflected light 230B travelling in the reverse direction along fibre portion 210. Accordingly, as flexible membrane 450 flexes and changes its configuration in accordance with pressure variations in the perilymph the intensity of reflected light 230B will vary. As would be appreciated by those skilled in the art, the Fabry Perot arrangement will in some circumstances have a higher sensitivity than the embodiment shown and described with respect to FIG. 2.

As will be appreciated by those skilled in the art, the Fabry-Perot arrangement shown in FIG. 4 is one embodiment of an optical interferometer based sensor. Other optical interferometer based sensors could be used in other embodiments.

The wavelength of the light used in these embodiments is not necessarily limited to the visible range of approximately 350 to 750 nanometers (nm), but rather may include ultraviolet, visible, infrared, far infrared or deep infrared light. For example, in certain embodiments, infrared light having wavelengths between about 750 nm and 1500 nm may be used. In other embodiments, light having longer or shorter wavelengths may also be used. In these circumstances, complementary components such as detectors and waveguide members would be selected to operate in the chosen wavelength band.

In another illustrative embodiment, two or more separate sensors are integrated into the electrode array at spaced apart locations. In one embodiment, a second sensor is positioned to measure pressure variations in the perilymph in the side wall of the stimulation assembly 140. In this manner, two separate measurements of perilymph pressure may be taken at different locations along the stimulation assembly 140.

With two separate measurements at different locations along the stimulation assembly 140, the cochlear implant can distinguish pressure waves (or other changes in pressure) associated with external acoustic sound waves from pressure waves (or other changes in pressure) associated with internal body noise. In some embodiments, body noise can be subtracted from the external sound signal based on measured phase difference between the two signals detected at different locations in the cochlea. PCT Publication No. WO 2009/102811 entitled "CANCELLATION OF BONE CONDUCTED SOUND IN A HEARING PROSTHESIS", filed on 11 Feb. 2009, and whose disclosure is herein incorporated by reference in its entirety, describes one example of a beam forming algorithm which may be advantageously employed with embodiments involving multiple sensing elements.

The tonotopic map in the cochlea results from the passive mechanical properties of the basilar membrane. This membrane, located at the interface between scala media and scala tympani, is thick and narrow at the base, thin and wide at the apex. The resulting stiffness gradient is primarily responsible for high frequency resonance peaks at the base and low frequency resonance peaks at the apical part of the cochlea. As a consequence, a set of sensing elements located along stimulation assembly 140 will provide pressure variation information of the perilymph over a much wider and more uniform spectrum.

In yet another illustrative embodiment, an electro-mechanical based sensor such as an electret, capacitive, or piezo based transducer may be employed in combination with stimulation assembly 140 instead of an optical based sensor. In this illustrative embodiment, standard electrical leads are employed instead of a fibre arrangement to both power and receive the electrical signals from the electro-mechanical based sensor, these electrical signals corresponding to the sensed variations in the pressure of the perilymph fluid.

Where multiple sensors are employed along stimulation assembly 140 then a combination of optical based sensors and electro-mechanical based sensors may be employed.

Figure 5:
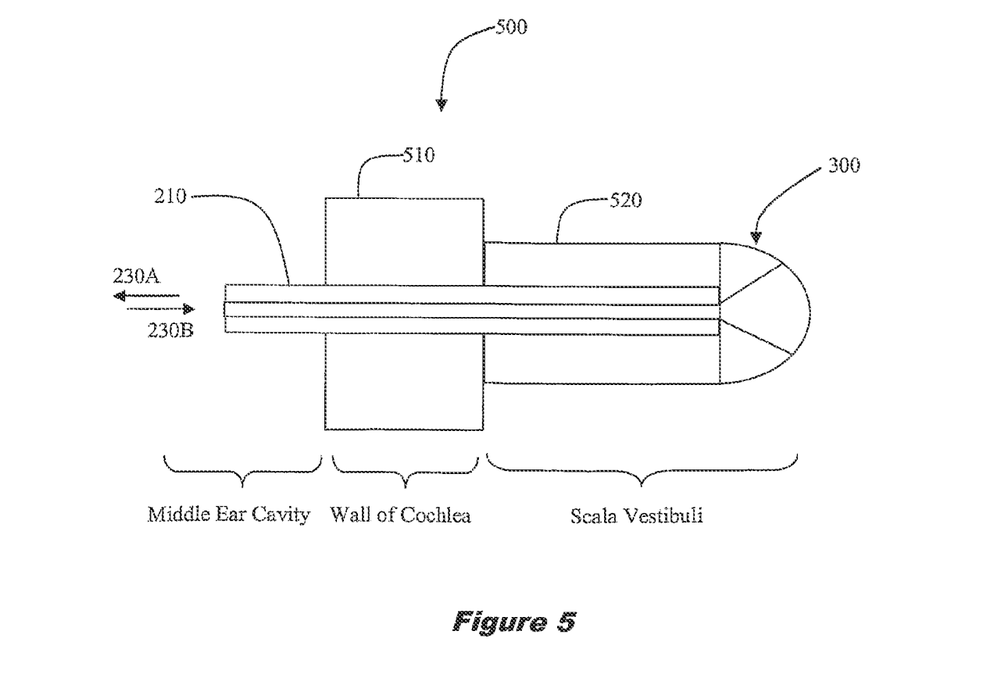
FIG. 5 is a figurative view of an implantable microphone in accordance with an illustrative embodiment.

While in the above embodiments the implant microphone is integrated with the stimulation assembly 140 as described previously, equally an implantable microphone in accordance with some embodiments may be implemented as a standalone module comprising an optical sensor located in the perilymph. Referring now to FIG. 5, there is shown an implantable microphone 500 in accordance with an illustrative embodiment. Implantable microphone 500 includes a fibre portion 210 terminating in an optical sensor 300 such as described previously. Implantable microphone 500 further includes a collar member 510 and a housing member 520 which are hermetically sealed around fibre portion 210 with housing member 520 forming a support for optical sensor 300. In another embodiment, a Fabry-Perot based optical sensor 400 such as described previously could also be employed.

In operation, housing member 520 is surgically inserted into the scala vestibuli so that the optical sensor 300 is in contact with the perilymph. On insertion of implantable microphone 500 into the scala vestibuli, collar member 35 having a cylindrical configuration seals into the opening made into the cochlea, thereby securing implantable microphone 500 in place.

Referring once again to FIG. 1, as would be appreciated by those skilled in the art an implantable microphone implemented in accordance with the embodiments described herein would only be applicable to those recipients of cochlear implants who still have a functioning middle ear that effectively transfers mechanical waves from the outer ear via the ossicles (i.e. the malleus 112, incus 113 and the stapes 114) of the middle ear to the inner ear or cochlea 116.

The middle ear effectively functions as an impedance transformer which matches the low impedance of the air to the high impedance of the perilymph located in the scala vestibuli and the scala tympani in the cochlea. As a result there is a pressure gain induced by the middle ear having an approximate factor of 30 dB at 1 kHz. This pressure gain may amplify air borne sound waves 107 received by the outer ear by a factor of about 22 in comparison with background body noise, effectively functioning as a noise filter resulting in significant signal to noise improvements over standard implantable microphones.

In another illustrative embodiment, a sensor for sensing pressure in the cochlea, such as physical interfaces with internal cochlear structures and variation in the perilymph may be employed to monitor physical contact and perilymph pressure during insertion of the stimulation assembly or electrode assembly into the cochlea.

During surgical implantation of a cochlear implant, the electrode array of the cochlear implant is inserted into the scala tympani of the cochlea. During the implantation procedure, surgeons try to avoid damage to the delicate structures within the cochlea. Inserting the electrode array into the cochlea can damage structures within the cochlea in multiple ways.

First, if the electrode array is not guided very carefully into the cochlea, the tip of the electrode array (or other parts of the electrode array) may damage or puncture the walls of the scala tympani or damage the osseous spiral lamina or modiolus (housing the spiral ganglion).

Second, even if the electrode array is guided into the cochlea so as to avoid contact with the inner walls of the cochlea, simply inserting the electrode array into the cochlea may increase the perilymph fluid pressure within the scala tympani. Increasing the perilymph fluid pressure within the scala tympani may in turn place pressure on the basilar membrane, which may stress the modiolus and damage the spiral ganglion.

Third, inserting the electrode array may cause fluid turbulence within the scala tympani which may damage any remaining functional hair cells that the implant recipient may have had. Avoiding damage to functional hair cells may be of particular importance for recipients of hybrid prostheses having an acoustic hearing aid component and a cochlear implant component, where the goal is for the recipient to hear lower acoustic frequencies with the acoustic hearing aid component and to hear higher acoustic frequencies with the cochlear implant component.

One way to avoid damage to the delicate cochlear structures during the insertion of the electrode array into a recipient's cochlea is to take pressure measurements inside the cochlea during the insertion procedure. In one embodiment, one or more sensors integrated into the stimulation assembly of the cochlear implant may be configured to measure pressure within the cochlea during the insertion procedure. The one or more sensors may be similar to the sensors shown and described herein with respect to FIGS. 2-4. For example, the one or more sensors may be optical sensors, optical interferometers, piezoresistive sensors, electro-mechanical sensors, or capacitive sensors. In some embodiments, at least one sensor may be located at the distal end of the electrode array (i.e., the end of the electrode array that is inserted into the cochlea). Additional sensors may be located at other positions along the electrode array.

The pressure measurements taken by the sensors may be sent or otherwise transmitted to one or more processors configured to correlate pressure measurements with corresponding damage conditions. In some embodiments, the pressure measurements from the sensors may be sent or transmitted to the one or more processors in substantially real-time. In some embodiments, the one or more processors may be associated with a computing device configured to aid the surgeon during the insertion procedure. The computing device may be any type of general-purpose or special-purpose computing device configured to execute computer-readable program code comprising instructions for correlating the pressure measurements with cochlear damage likelihoods or damage conditions.

The computing device may receive a plurality of cochlear pressure measurements from sensors integrated into the stimulation assembly as described herein. The computing device may determine whether the cochlear pressure measurements correspond to one or more damage conditions. In some embodiments, the computing device may determine whether one or more cochlear pressure measurements correspond to a damage condition by comparing the pressure measurements with a lookup table of pressure measurements that includes a correlation of pressure measurements that indicate actual or potential damage to a cochlea.

For example, one damage condition may be based on one of the sensors physically touching an internal cochlear structure. Another damage condition may be based on perilymph fluid pressure exceeding a threshold pressure. Still another damage condition may be based on a rate of change of measured perilymph fluid pressure that exceeds a threshold rate of change. Still another damage condition may be based on a physical contact of one sensor with a cochlear structure combined with a perilymph fluid pressure that exceeds a threshold pressure. Other damage conditions based on other pressure measurements or combinations of pressure measurements could be used as well.

If the computing device determines that one or more of the pressure measurements correspond to a damage condition, the computing device may generate an indication to alert the surgeon that a damage condition has been detected. The alert may be one or both of an audible alarm or a graphical indication displayed via a graphical user interface. For embodiments that may employ multiple sensors, the indication (audible or graphical) may also indicate which of the sensors detected the damage condition.

When the computing device alerts the surgeon to a particular damage condition, the surgeon can then take corrective action to prevent or avoid further damage. For example, a pressure measurement may indicate that a sensor has likely touched a cochlear structure, such as the walls of the scala tympani, the osseous spiral lamina, or the modiolus. If a pressure measurement indicates that a sensor has likely touched a cochlear structure, and if the computing device then alerts the surgeon of the corresponding damage condition, then the surgeon can re-position the electrode array so as to avoid further contact with the internal cochlear structure.

Similarly, a pressure measurement may indicate that perilymph fluid pressure within the cochlea is sufficiently high (or that a rate of change in the perilymph pressure is sufficiently great enough) to stress internal cochlear structures. In response to a corresponding indication, the surgeon may retract the electrode array to reduce the perilymph pressure. The surgeon may also take other steps to reduce the perilymph pressure, such as releasing some the perilymph fluid from the cochleostomy point where the electrode array is inserted into the cochlea. Additionally, by monitoring the perilymph pressure, a surgeon is able to minimise potential damage to hair cells or to the cochlear structure by adjusting the amount or rate of insertion to reduce perilymph pressure.

It will be understood that the term "comprise" and any of its derivatives (eg. comprises, comprising) as used in this specification is to be taken to be inclusive of features to which it refers, and is not meant to exclude the presence of any additional features unless otherwise stated or implied.

The reference to any prior art in this specification is not, and should not be taken as, an acknowledgement of any form of suggestion that such prior art forms part of the common general knowledge.

Although illustrative embodiments have been described in the foregoing detailed description, it will be understood that the claims are not limited to the embodiments disclosed.

What is claimed is:

1. A method comprising:
   taking a first set of pressure wave measurements within a cochlea with a first optical sensor, wherein the first optical sensor is a component of a stimulation assembly comprising an electrode array;
   taking a second set of pressure wave measurements within the cochlea with a second sensor, wherein the second sensor is a component of the stimulation assembly;
   generating a first set of electrical stimulation signals based at least in part on the first set of pressure wave measurements and the second set of pressure wave measurements, wherein generating the first set of electrical stimulation signals comprises (i) determining a phase difference between the first set of pressure wave measurements and the second set of pressure wave measurements and (ii) generating the first set of electrical stimulation signals based on the determined phase difference; and
   applying the first set of electrical stimulation signals to the cochlea via the electrode array of the stimulation assembly.

2. A method comprising:
   receiving one or more first cochlear pressure measurements from a first optical sensor, wherein the first optical sensor is a component of a stimulation assembly of a cochlear implant comprising an electrode array;
   determining whether the one or more first cochlear pressure measurements corresponds to at least one cochlea damage condition based on determining that a rate of change of measured perilymph fluid pressure exceeds a threshold; and
   generating an indication in response to determining that the one or more first cochlear pressure measurements corresponds to the at least one cochlea damage condition.

3. The method of claim 2, further comprising:
   receiving one or more second cochlear pressure measurements from a second sensor, wherein the second sensor is a component of the stimulation assembly of the cochlear implant;
   determining whether the one or more second cochlear pressure measurements corresponds to the at least one cochlea damage condition; and
   generating an indication in response to determining that the one or more second cochlear pressure measurements corresponds to the at least one cochlea damage condition.

4. The method of claim 2, wherein the indication includes at least one of an audible alarm and a graphical indication displayed via a graphical user interface.

5. The method of claim 3, wherein the indication includes at least one of an audible alarm and a graphical indication displayed via a graphical user interface, and wherein the indication is based at least in part on whether the at least one cochlea damage condition is based on the first or second cochlear pressure measurements.

6. A method comprising:
   taking a first set of pressure wave measurements within a cochlea with a first sensor, wherein the first sensor is a component of a stimulation assembly comprising an electrode array;
   taking a second set of pressure wave measurements within the cochlea with a second sensor, wherein the second sensor is a component of the stimulation assembly;
   determining a phase difference between the first set of pressure wave measurements and the second set of pressure wave measurements;
   generating a set of electrical stimulation signals based on the determined phase difference; and
   applying the set of electrical stimulation signals to the cochlea via the electrode array of the stimulation assembly.

7. A method comprising:
   receiving one or more perilymph pressure measurements from a sensor, wherein the sensor is a component of a stimulation assembly of a cochlear implant comprising an electrode array;
   determining whether a rate of change of measured perilymph fluid pressure exceeds a threshold; and
   indicating a cochlea damage condition in response to determining that the rate of change of measured perilymph fluid pressure exceeds a threshold.

* * * * *